United States Patent
Williams et al.

(10) Patent No.: US 8,246,909 B2
(45) Date of Patent: Aug. 21, 2012

(54) AUTOMATED ENDOSCOPE REPROCESSOR GERMICIDE CONCENTRATION MONITORING SYSTEM AND METHOD

(75) Inventors: Hal Williams, San Clemente, CA (US); Yan Fang, Irvine, CA (US); Richard Jackson, Huntington Beach, CA (US)

(73) Assignee: Ethicon, Inc., Somerville, NJ (US)

( * ) Notice: Subject to any disclaimer, the term of this patent is extended or adjusted under 35 U.S.C. 154(b) by 494 days.

(21) Appl. No.: 11/855,291

(22) Filed: Sep. 14, 2007

(65) Prior Publication Data

US 2009/0060798 A1  Mar. 5, 2009

(51) Int. Cl.
*A61L 9/00* (2006.01)
*A61L 2/00* (2006.01)
*B08B 9/00* (2006.01)
*B08B 3/00* (2006.01)
*G01M 3/20* (2006.01)
*B01D 46/00* (2006.01)

(52) U.S. Cl. ............... 422/68.1; 422/1; 422/28; 422/32; 422/82.05; 422/119; 422/292; 134/22.13; 134/22.16; 134/22.19; 134/94.1; 134/109; 134/166 R; 73/1.02; 73/36; 73/53.01; 73/863.71; 95/68; 95/273; 210/348

(58) Field of Classification Search ................ 422/1, 28, 422/32, 68.1, 82.05, 119, 292; 134/22.13, 134/22.16, 22.19, 94.1, 109, 166 R; 73/1.02, 73/36, 53.01, 863.71; 95/68, 273; 210/348
See application file for complete search history.

(56) References Cited

U.S. PATENT DOCUMENTS

| 5,858,305 | A | 1/1999 | Malchesky |
| 6,068,815 | A * | 5/2000 | Oberleitner et al. ............ 422/28 |
| 6,297,505 | B1 | 10/2001 | Frandsen et al. |
| 6,783,767 | B2 | 8/2004 | Shroot et al. |
| 6,884,392 | B2 | 4/2005 | Malkin et al. |
| 7,138,087 | B1 | 11/2006 | Malkin et al. |
| 7,291,649 | B2 | 11/2007 | Zhu et al. |
| 2003/0025909 | A1 * | 2/2003 | Hallstadius .................. 356/436 |
| 2005/0066812 | A1 * | 3/2005 | Vesper et al. ..................... 95/46 |
| 2006/0045798 | A1 * | 3/2006 | Wu et al. ......................... 422/28 |

FOREIGN PATENT DOCUMENTS

| EP | 0884115 B1 | 1/2006 |
| GB | 2402066 A | 12/2004 |
| WO | WO 98/16260 A1 | 4/1998 |
| WO | WO 98/51816 A2 | 11/1998 |

OTHER PUBLICATIONS

McDonnell, Gerald and A. Denver Russell, "Antiseptics and Disinfectants: Activity, Action, and Resistance", Clinical Microbiology Reviews, Jan. 1999, vol. 12, No. 1, pp. 147-179.
European Search Report for European Application No. 06254458.0 dated Jan. 11, 2007.

* cited by examiner

*Primary Examiner* — Jill Warden
*Assistant Examiner* — Monzer Chorbaji

(57) ABSTRACT

A method measures a property of a germicidal solution in an endoscope processor spectroscopically by placing a quantity of the solution into a cuvette and passing a light therethrough. A reservoir receives a quantity of the solution and bubbles are filtered out via a cross-flow filter prior to putting a sample therefrom into the cuvette for measuring.

22 Claims, 7 Drawing Sheets

Normal Mode

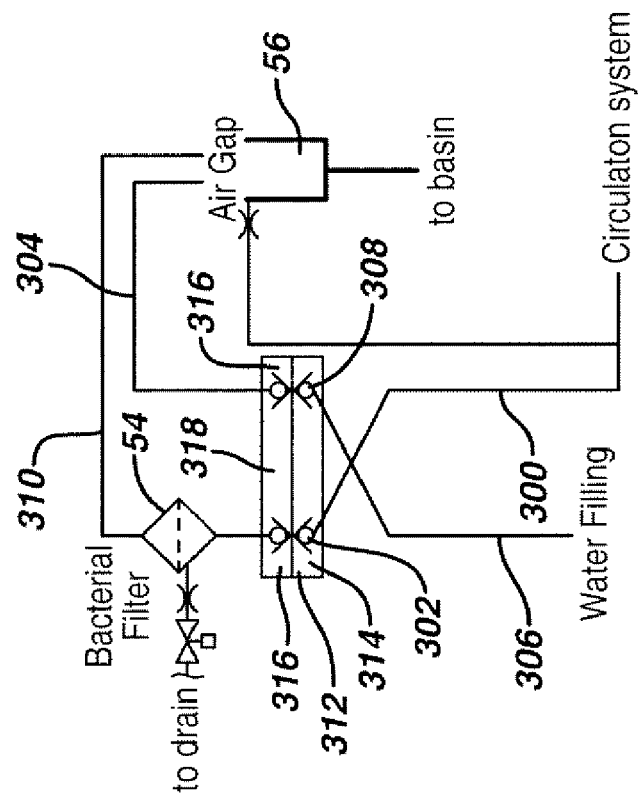
FIG. 4B  Self-Disinfection Mode
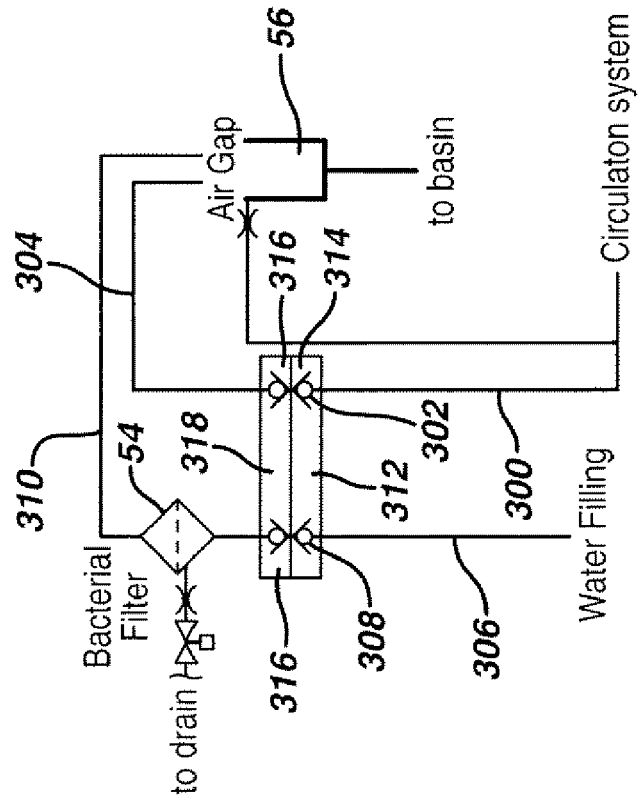
FIG. 4A  Normal Mode

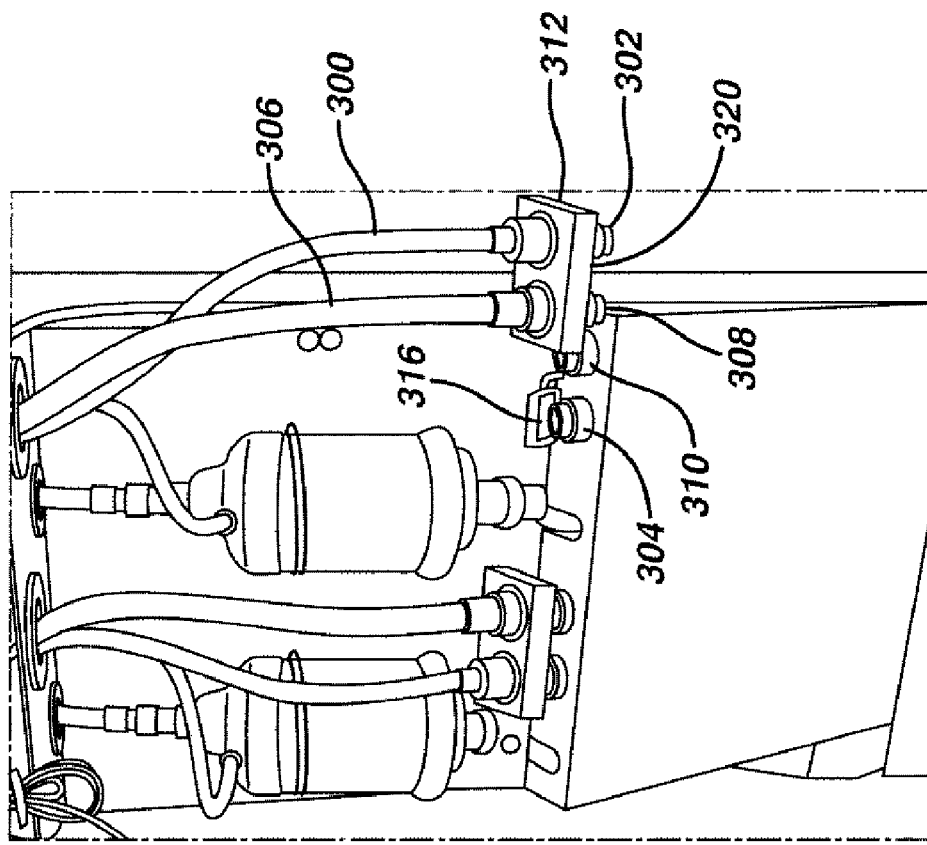
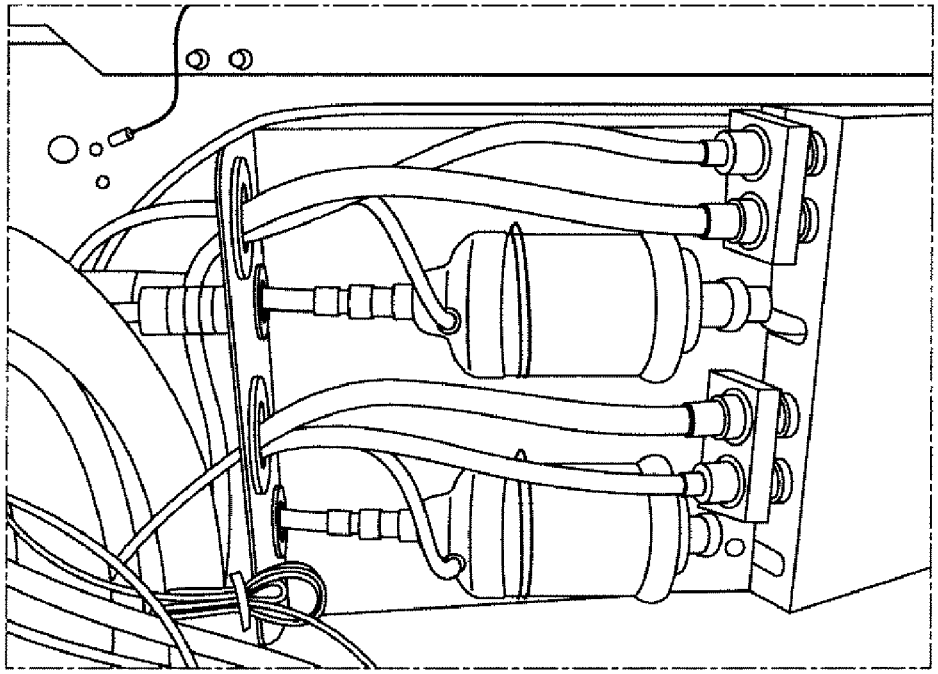
FIG. 5

Functional Diagram - Optical

US 8,246,909 B2

AUTOMATED ENDOSCOPE REPROCESSOR GERMICIDE CONCENTRATION MONITORING SYSTEM AND METHOD

BACKGROUND OF THE INVENTION

The present invention relates to the decontamination arts including the sterilization arts. It finds particular application in conjunction with the decontamination of medical devices, especially medical devices such as endoscopes and other devices having channels or lumens that must be decontaminated after use.

Endoscopes and similar medical devices having channels or lumens formed therethrough are being used on an ever increasing basis in the performance of medical procedures. The popularity of these devices has led to calls for improvements in the decontamination of these devices between use, both in terms of the speed of the decontamination and the effectiveness of the decontamination.

One popular method for cleaning and disinfection or sterilization of such endoscopes employs an automated endoscope reprocessor which both washes and then disinfects or sterilizes the endoscope. Typically such a unit comprises a basin with a selectively opened and closed cover member to provide access to the basin. Pumps connect to various channels through the endoscope to flow fluid therethrough and an additional pump flows fluid over the exterior surfaces of the endoscope. Typically, a detergent washing cycle is followed by rinsing and then a sterilization or disinfection cycle employing a liquid germicidal solution and rinse.

To ensure proper processing of the endoscope, it is important to assess whether the germicidal solution has a proper concentration. Manual methods exist for such an assessment but during an automatic processing cycle it is desired to perform such analysis automatically. Certain germicides, such as aldehydes, can be measured by passing a light through a sample. In such process the measurement can be affected by the presence of bubbles in the sample and it is desired to eliminate such bubbles. If a traditional filter is employed it is of concern that bubbles may accumulate against the filter and create a vapor barrier to fluid passing therethrough. A vent may be employed, but such venting is cumbersome in an automatic processing cycle. The present invention addresses these and other limitations of the prior art.

SUMMARY OF THE INVENTION

A method according to the present invention provides for measuring concentration of a germicide in an instrument processor. The method comprises the steps of: directing a flow of fluid containing the germicide through a bubble filter to obtain a bubble free sample of the fluid; directing the sample of the fluid into a sample chamber having clear sides; and passing light of a known intensity and wavelength through the chamber and sample therein, detecting the light passing therethrough with a sensor and based upon its output determining a concentration of the germicide in the sample. The bubble filter comprises a cross-flow filter wherein a flow of fluid passes along a membrane and a portion of the flow passes through the membrane to provide the sample whereby to prevent accumulation of bubbles against the membrane.

Preferably, the germicide comprises ortho-phthalaldehyde. Preferably, the light is at about 254 nm. More preferably, at least 90 percent of the light's spectra is within 450 nm plus or minus 1 nm.

Preferably, the membrane is hydrophilic and has a maximum pore size of 0.2 µm, and more preferably of 0.45 µm.

Preferably, the method further comprises the step of aborting an instrument processing cycle in the instrument processor if the concentration is below a predetermined level, as for instance wherein the germicide comprises ortho-phthalaldehyde and the predetermined level is 0.059% or lower. The method further preferably comprises the step of aborting an instrument processing cycle in the instrument processor if the concentration is above 0.1% or alternatively above 0.85%.

The flow of fluid passing along the membrane carries bubbles away from an upstream side of the membrane.

An instrument processor according to the present invention comprises an enclosure for holding an instrument; a fluid distribution system for delivering a fluid containing a germicide to the instrument within the enclosure; and a germicide concentration measuring subsystem. This subsystem comprises a bubble filter connected to the fluid distribution system; a sample chamber connected to a sample outlet of the bubble filter; a light source for passing a light of known intensity and wavelength through a sample of the fluid in the sample chamber; a sensor for measuring light passing through the sample; and a control system for determining the concentration of the germicide in the sample based upon the light arriving at the sensor. The bubble filter comprises a cross-flow filter wherein a flow of fluid passes along a membrane and a portion of the flow passes through the membrane to provide the sample whereby to prevent accumulation of bubbles against the membrane.

BRIEF DESCRIPTION OF THE DRAWINGS

The invention may take form in various components and arrangements of components and in various steps and arrangements of steps. The drawings are for purposes of illustrating preferred embodiments only, and are not to be construed as limiting the invention.

FIGS. 4a and 4b are diagrammatic illustrations of a fresh water supply system in both a normal mode and a filter sterilization mode, respectively; and FIG. 5 is a front elevation view of the fresh water supply system of FIGS. 4a and 4b;

DETAILED DESCRIPTION OF THE PREFERRED EMBODIMENT

Figure 1:
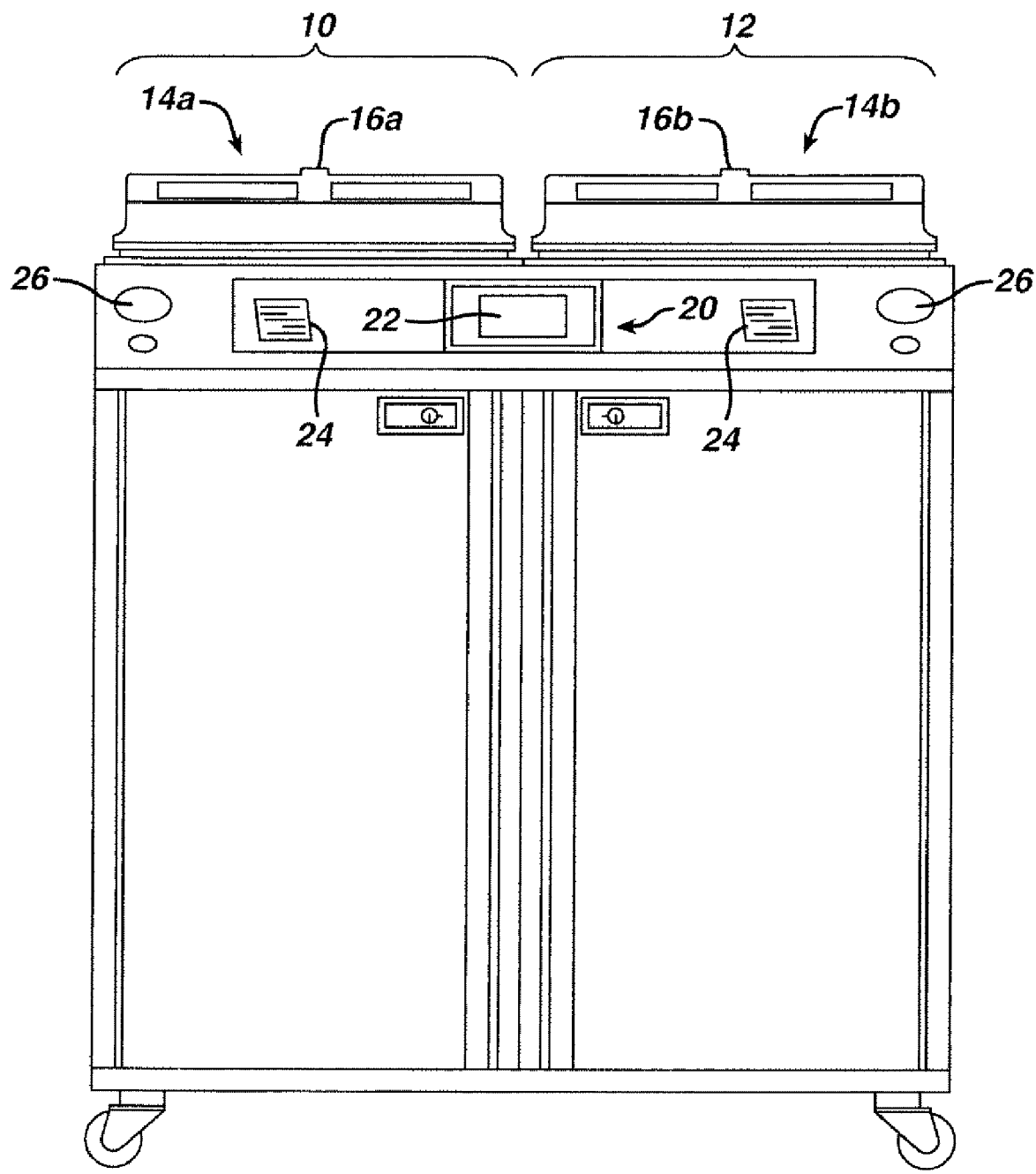
FIG. 1 is a front elevational view of a decontamination apparatus in accordance with the present invention.
Figure 2:
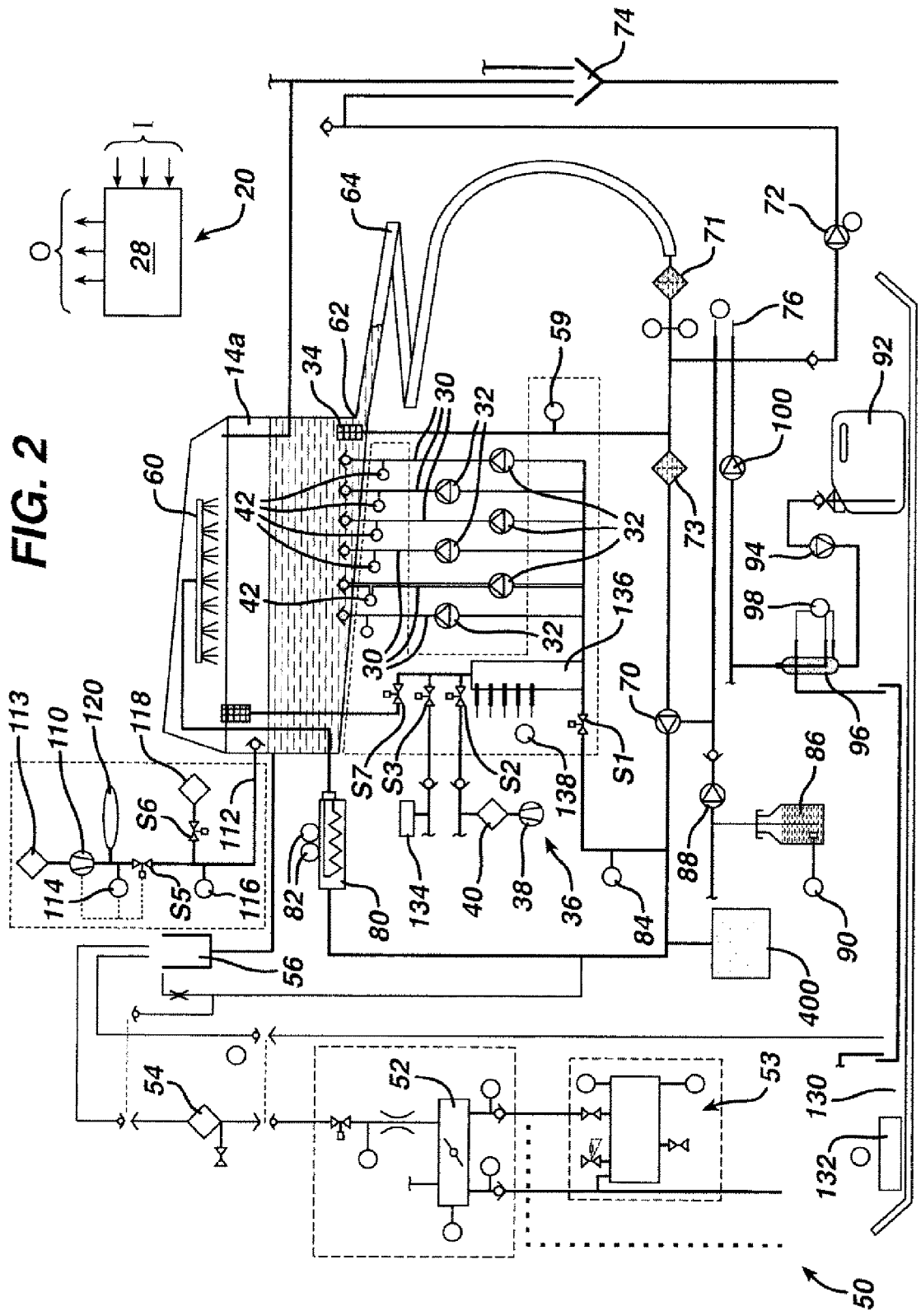
FIG. 2 is a diagrammatic illustration of the decontamination apparatus shown in FIG. 1, with only a single decontamination basin shown for clarity.

FIG. 1 shows a decontamination apparatus for decontaminating endoscopes and other medical devices which include channels or lumens formed therethrough; FIG. 2 shows the apparatus in block diagram form. The decontamination apparatus generally includes a first station 10 and a second station 12 which are at least substantially similar in all respects to provide for the decontamination of two different medical devices simultaneously or in series. First and second decontamination basins 14a, 14b receive the contaminated devices. Each basin 14a, 14b is selectively sealed by a lid 16a, 16b, respectively, preferably in a microbe-blocking relationship to prevent the entrance of environmental microbes into the basins 14a, 14b during decontamination operations. The lids can include a microbe removal or HEPA air filter formed therein for venting.

A control system 20 includes one or more microcontrollers, such as a programmable logic controller (PLC), for controlling decontamination and user interface operations. Although one control system 20 is shown herein as controlling both decontamination stations 10, 12, those skilled in the art will recognize that each station 10, 12 can include a dedicated control system. A visual display 22 displays decontamination parameters and machine conditions for an operator and at least one printer 24 prints a hard copy output of the decontamination parameters for a record to be filed or attached to the decontaminated device or its storage packaging. The visual display 22 is preferably combined with a touch screen input device. Alternatively, a keypad or the like is provided for input of decontamination process parameters and for machine control. Other visual gauges 26 such as pressure meters and the like provide digital or analog output of decontamination or medical device leak testing data.

FIG. 2 diagrammatically illustrates one station 10 of the decontamination apparatus. Those skilled in the art will recognize that the decontamination station 12 is preferably similar in all respects to the station 10 illustrated in FIG. 2. However, the station 12 has not been shown in FIG. 2 for clarity. Further, the decontamination apparatus can be provided with a single decontamination station or multiple stations.

The decontamination basin 14a receives an endoscope 200 (see FIG. 3) or other medical device therein for decontamination. Any internal channels of the endoscope 200 are connected with flush lines 30. Each flush line 30 is connected to an outlet of a pump 32. The pumps 32 are preferably peristaltic pumps or the like that pump fluid, such as liquid and air, through the flush lines 30 and any internal channels of the medical device. Specifically, the pumps 32 either can draw liquid from the basin 14a through a filtered drain 34 and a first valve S1, or can draw decontaminated air from an air supply system 36 through a valve S2. The air supply system 36 includes a pump 38 and a microbe removal air filter 40 that filters microbes from an incoming air stream. It is preferable that each flush line 30 be provided with a dedicated pump 32 to ensure adequate fluid pressure and to facilitate the individual monitoring of the fluid pressure in each flush line 30. A pressure switch or sensor 42 is in fluid communication with each flush line 30 for sensing excessive pressure in the flush line. Any excessive pressure sensed is indicative of a partial or complete blockage, e.g., by bodily tissue or dried bodily fluids, in a device channel to which the relevant flush line 30 is connected. The isolation of each flush line 30 relative to the others allows the particular blocked channel to be easily identified and isolated, depending upon which sensor 42 senses excessive pressure.

The basin 14a is in fluid communication with a water source 50 such as a utility or tap water connection including hot and cold inlets and a mixing valve 52 flowing into a break tank 56. A microbe removal filter 54, such as a 0.2 µm or smaller absolute pore size filter, decontaminates the incoming water which is delivered into the break tank 56 through the air gap to prevent backflow. A pressure type level sensor 59 monitors liquid levels within the basin 14a. An optional water heater 53 can be provided if an appropriate source of hot water is not available.

The condition of the filter 54 can be monitored by directly monitoring the flow rate of water therethrough or indirectly by monitoring the basin fill time using a float switch or the like. When the flow rate drops below a select threshold, this indicates a partially clogged filter element that requires replacement.

A basin drain 62 drains liquid from the basin 14a through an enlarged helical tube 64 into which elongated portions of the endoscope 200 can be inserted. The drain 62 is in fluid communication with a recirculation pump 70 and a drain pump 72. The recirculation pump 70 recirculates liquid from the basin drain 62 to a spray nozzle assembly 60 which sprays the liquid into the basin 14a and onto the endoscope 200. Coarse and fine screens 71 and 73, respectively, filter out particles in the recirculating fluid. The drain pump 72 pumps liquid from the basin drain 62 to a utility drain 74. A level sensor 76 monitors the flow of liquid from the pump 72 to the utility drain 74. The pumps 70 and 72 can be simultaneously operated such that liquid is sprayed into the basin 14a while it is being drained to encourage the flow of residue out of the basin and off of the device. Of course, a single pump and a valve assembly could replace the dual pumps 70, 72.

An inline heater 80, with temperature sensors 82, downstream of the recirculation pump 70 heats the liquid to optimum temperatures for cleaning and disinfection. A pressure switch or sensor 84 measures pressure downstream of the circulation pump 70.

Detergent solution 86 is metered into the flow upstream of the circulation pump 70 via a metering pump 88. A float switch 90 indicates the level of detergent available. Typically, only a small amount of disinfectant 92 is required. To more accurately meter this, a dispensing pump 94 fills a pre-chamber 96 under control of a hi/low level switch 98 and of course the control system 20. A metering pump 100 meters a precise quantity of disinfectant as needed.

Endoscopes and other reusable medical devices often include a flexible outer housing or sheath surrounding the individual tubular members and the like that form the interior channels and other parts of the device. This housing defines a closed interior space, which is isolated from patient tissues and fluids during medical procedures. It is important that the sheath be maintained intact, without cuts or other holes that would allow contamination of the interior space beneath the sheath. Therefore, the decontamination apparatus includes means for testing the integrity of such as sheath.

An air pump, either the pump 38 or another pump 110, pressurizes the interior space defined by the sheath of the device through a conduit 112 and a valve S5. Preferably, a HEPA or other microbe-removing filter 113 removes microbes from the pressurizing air. An overpressure switch 114 prevents accidental over pressurization of the sheath. Upon full pressurization, the valve S5 is closed and a pressure sensor 116 looks for a drop in pressure in the conduit 112 which would indicate the escape of air through the sheath. A valve S6 selectively vents the conduit 112 and the sheath through an optional filter 118 when the testing procedure is complete. An air buffer 120 smoothes out pulsation of pressure from the air pump 110.

Preferably, each station 10 and 12 each contain a drip basin 130 and spill sensor 132 to alert the operator to potential leaks.

An alcohol supply 134 controlled by a valve S3 can supply alcohol to the channel pumps 32 after rinsing steps to assist in removing water from the endoscope channels.

Flow rates in the supply lines 30 can be monitored via the channel pumps 32 and the pressure sensors 42. The channels pumps 32 are peristaltic pumps which supply a constant flow. If one of the pressure sensors 42 detects too high a pressure the associated pump 32 cycles off. The flow rate of the pump 32 and its percentage on time provide a reasonable indication of the flow rate in an associated line 30. These flow rates are monitored during the process to check for blockages in any of the endoscope channels. Alternatively, the decay in the pressure from the time the pump 32 cycles off can also be used to estimate the flow rate, with faster decay rates being associated with higher flow rates.

A more accurate measurement of flow rate in an individual channel may be desirable to detect more subtle blockages. A metering tube 136 having a plurality of level indicating sensors 138 fluidly connects to the inputs of the channel pumps 32. One preferred sensor arrangement provides a reference connection at a low point in the metering tube and a plurality of sensors 138 arranged vertically thereabove. By passing a current from the reference point through the fluid to the sensors 138 it can be determined which sensors 138 are immersed and therefore determine the level within the metering tube 136. Other level sensing techniques can be applied here. By shutting valve S1 and opening a vent valve S7 the channel pumps 32 draw exclusively from the metering tube. The amount of fluid being drawn can be very accurately determined based upon the sensors 138. By running each channel pump in isolation the flow therethrough can be accurately determined based upon the time and the volume of fluid emptied from the metering tube.

In addition to the input and output devices described above, all of the electrical and electromechanical devices shown are operatively connected to and controlled by the control system 20. Specifically, and without limitation, the switches and sensors 42, 59, 76, 84, 90, 98, 114, 116, 132 and 136 provide input I to the microcontroller 28 which controls the decontamination and other machine operations in accordance therewith. For example, the microcontroller 28 includes outputs O that are operatively connected to the pumps 32, 38, 70, 72, 88, 94, 100, 110, the valves S1-S7, and the heater 80 to control these devices for effective decontamination and other operations.

Figure 3:
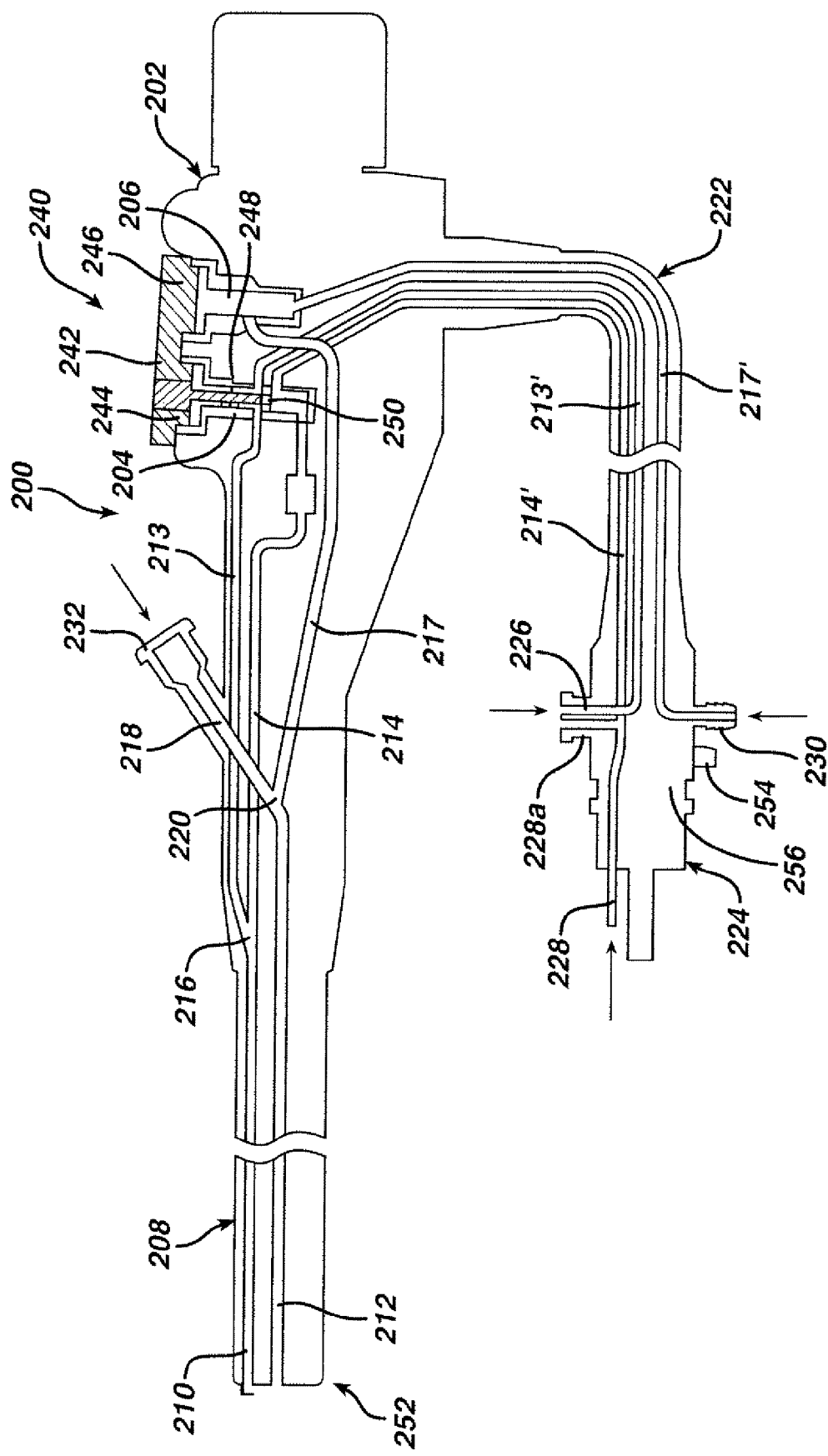
FIG. 3 is a cut-away view of an endoscope suitable for processing in the decontamination apparatus of FIG. 1.

Turning also to FIG. 3, an endoscope 200 has a head part 202, in which openings 204 and 206 are formed, and in which, during normal use of the endoscope 200, an air/water valve and a suction valve are arranged. A flexible insertion tube 208 is attached to the head part 202, in which tube a combined air/water channel 210 and a combined suction/biopsy channel 212 are accommodated.

A separate air channel 213 and water channel 214, which at the location of a joining point 216 merge into the air/water channel 210, are arranged in the head part 202. Furthermore, a separate suction channel 217 and biopsy channel 218, which at the location of the joining point 220 merge into the suction/biopsy channel 212, are accommodated in the head part 202.

In the head part 202, the air channel 213 and the water channel 214 open into the opening 204 for the air/water valve. The suction channel 217 opens into the opening 206 for the suction valve. Furthermore, a flexible feed hose 222 connects to the head part 202 and accommodates channels 213', 214' and 217' which via the openings 204 and 206, are connected to the air channel 213, the water channel 214 and the suction channel 217, respectively. In practice, the feed hose 222 is also referred to as the light-conductor casing.

The mutually connecting channels 213 and 213', 214 and 214', 217 and 217' will be referred to below overall as the air channel 213, the water channel 214 and the suction channel 217.

A connection 226 for the air channel 213, connections 228 and 228a for the water channel 214 and a connection 230 for the suction channel 217 are arranged on the end section 224 (also referred to as the light conductor connector) of the flexible hose 222. When the connection 226 is in use, connection 228a is closed off. A connection 232 for the biopsy channel 218 is arranged on the head part 202.

A channel separator 240 is shown inserted into the openings 204 and 206. It comprises a body 242, and plug members 244 and 246 which occlude respectively openings 204 and 206. A coaxial insert 248 on the plug member 244 extends inwardly of the opening 204 and terminates in an annular flange 250 which occludes a portion of the opening 204 to separate channel 213 from channel 214. By connecting the lines 30 to the openings 226, 228, 228a, 230 and 232, liquid for cleaning and disinfection can be flowed through the endoscope channels 213, 214, 217 and 218 and out of a distal tip 252 of the endoscope 200 via channels 210 and 212. The channel separator 240 ensures the such liquid flows all the way through the endoscope 200 without leaking out of openings 204 and 206 and isolates channels 213 and 214 from each other so that each has its own independent flow path. One of skill in the art will appreciate that various endoscopes having differing arrangements of channels and openings will likely require modifications in the channel separator 240 to accommodate such differences while occluding ports in the head 202 and keeping channels separated from each other so that each channel can be flushed independently of the other channels. Otherwise a blockage in one channel might merely redirect flow to a connected unblocked channel.

A leakage port 254 on the end section 224 leads into an interior portion 256 of the endoscope 200 and is used to check for the physical integrity thereof, namely to ensure that no leakage has formed between any of the channels and the interior 256 or from the exterior to the interior 256.

Some endoscope channels, such as the suction/biopsy channel 212 in some endoscopes have internal diameters which are too large to adequately assess their connection status with the metering tube 136. For these channels, pressure pulses induced by the pumps 32 can be examined to assess proper connection.

Connection is made at connection 230 to the suction channel 217 and at connection 232 for the suction/biopsy channel 212. Each of these connections is made via one of the flexible tubes 108. By examining the pressure measured at the corresponding pressure sensor 42 the connection status between the connections 232, 230 and their corresponding flush line outlet 31 can be examined.

For instance, if the pump 32 in the flush line 30 connected (via one of the tubes 108) to the connection 230 is turned off and the pressure sensor 42 in this same flush line 30 is read, pressure pulses from the pump 32 in the flush line 30 connected to the connection 232 should be read. The suction channel 217 and suction/biopsy channel 212 meet internally inside the endoscope 200 putting the connections 230 and 232 in fluid communication with each other. The pumps 32 are peristaltic pumps which produce a known pressure wave at about 10 Hz, which of course will vary with the speed of the pump. Other methods could be used to induce the pressure pulses or waves, but the pumps 32 are quite convenient. Preferably the readings from the pressure sensor 42 are filtered electronically to remove noise above and below the target frequency (in the present example 10 Hz). If a significant pressure signal is not measured at the target frequency that indicates that one of the connections is not made; proper connection must be made between the flexible tube 108 and connection 230, and at the opposite end of that flexible tube and the appropriate outlet 31, as well as between a second of the flexible tubes 108 and the connection 232 and at the opposite end of this flexible tube and the appropriate outlet 31.

It is not necessary to stop one of the pumps 32 to assess proper connection. The pumps will never be in perfect synchronization and at the exact same frequency and therefore with two of the pumps running through the connections 230 and 232 a beat frequency formed by the difference in each pump's frequency should be detectable at each of the pressure sensors 42 associated therewith. Only one of the pressure sensors 42 need be measured.

Readings at the pressure sensors 42 can also detect improper connection at either connection 230, connection 232, or some other connection, by listening for the reflection of the pressure waves. Here, the pressure sensor 42 in the flush line 30 connected via a flexible tube 108 to connection 232 would be listening for reflections from the pump 32 in that flush line 30. These reflections would come from any discontinuities in the path between the pump 32 and where the biopsy/suction channel 212 leaves the distal end of the insertion tube 208. When properly connected, the major echo should come from the open end of the channel 212 at the distal end of the insertion tube 208. Other reflections would come from the connection between the flexible tube 108 and the connection 232, the connection between the flexible tube 108 and the outlet 31, the intersection of channels 217 and 212 and perhaps other surfaces and discontinuities therein. When one end of the tube 108 is not connected a different echo signature would be presented.

Echo signatures from different types of endoscopes 200 can be stored in the controller 28 and compared with the measured results to determine whether it matches that of a properly connected endoscope. Signatures for a disconnection at the connection 232 or a disconnection at the outlet 31 could also be stored for comparison. Different types and configurations of the flexible tube 108 may be used for different endoscope types which should be taken into consideration. Similar signatures can be stored for the connection 230 or any other connection on the endoscope. Although it is possible to prepare and store signatures for individual endoscope models, there is sufficient similarity among related endoscopes that signatures for broad classes of endoscopes could be used. If signatures for each endoscope model are stored, they could also be used to verify that the proper endoscope model has been entered into the controller.

Turning primarily also now to FIGS. 4A and 4B, and also to FIG. 5, the filter 54, break tank 56 (which forms the air gap to isolate the water source 50 from the rest of the system) and associated plumbing are shown. A recirculation line proximal portion 300 connects, via a connector 302, to a recirculation line distal portion 304, which in turn flows into the break tank 56. Similarly, a water supply line proximal portion 306 connects, via a connector 308, to a water supply line distal portion 310, which contains the filter 54 and which also then flows into the break tank 56. The connectors 302 and 308 are joined together by a carrier bar 312.

The filter 54 requires periodic disinfection. In many reprocessors such a filter is removed from the system and treated in an autoclave. Performing this chore is tedious. The system can circulate disinfectant 92, yet this can not merely be plumbed into the lines upstream of the filter 54 as that would violate the integrity of the air gap at the break tank 56 which protects the water supply from the fluids within the system. Applicants have solved this dilemma with the connectors 302 and 308 on the carrier bar 312. By pulling the carrier bar 312 and reversing the connections from their normal mode as shown in FIG. 4A and placing them into a self-disinfection mode as shown in FIG. 4B, disinfectant 92 can be supplied to the filter 54 without violating the integrity of the air gap and while still having the water source 50 connected to the break tank 56 whereby to supply rinse water after the filter 54 has been disinfected. In the self-disinfecting mode the recirculation line proximal portion 300 connects to the water supply line distal portion 310, and thus to the filter 54, and the water supply line proximal portion 306 connects to the recirculation line distal portion 304.

By running the system in self-disinfection mode, either a full cycle, or an abbreviated cycle consisting of circulating disinfectant 92 followed by a rinse with water (after reverting the connections to the normal mode), the downstream portion of the filter 54 and the water supply line distal portion 310 are disinfected and then rinsed. Alternatively, heated water, preferably above 70° C. or 80° C. can be circulated through the filter 54, with the extra heat to achieve this temperature coming from the heater 80.

A magnet 314 on the carrier bar 312 and a sensors 316 on a housing portion 318 which the carrier bar 312 abuts when connected provides an indication to the controller 28 of which mode, normal or self-disinfection, the system is in and will not allow a normal instrument processing cycle when in self-disinfection mode and vice versa. It can also detect when the carrier bar 312 is not present indicating two open connections and similarly will prevent cycles from being run in this condition. Visual indicia 320 are also provided on the carrier bar 312, such as green showing for normal mode and red showing for self-disinfection mode. FIG. 5 shows two sets of carrier bars 312 etc. as this set-up is repeated for the second station 12.

In one preferred embodiment, not shown in the drawings, reversal of connectors 302 and 308 is automated. This could be achieved through a motor controlled rotary spool valve having a first pair of passages therethrough to connect the water supply line proximal portion 306 to its distal portion 310 and the recirculation line proximal portion 300 to its distal portion 304, and upon rotation of the spool having a second set of passages therethrough to connect the water supply proximal portion 306 to the recirculation line distal portion 304 and the recirculation proximal portion 300 to the water supply line distal portion 310.

Figure 6:
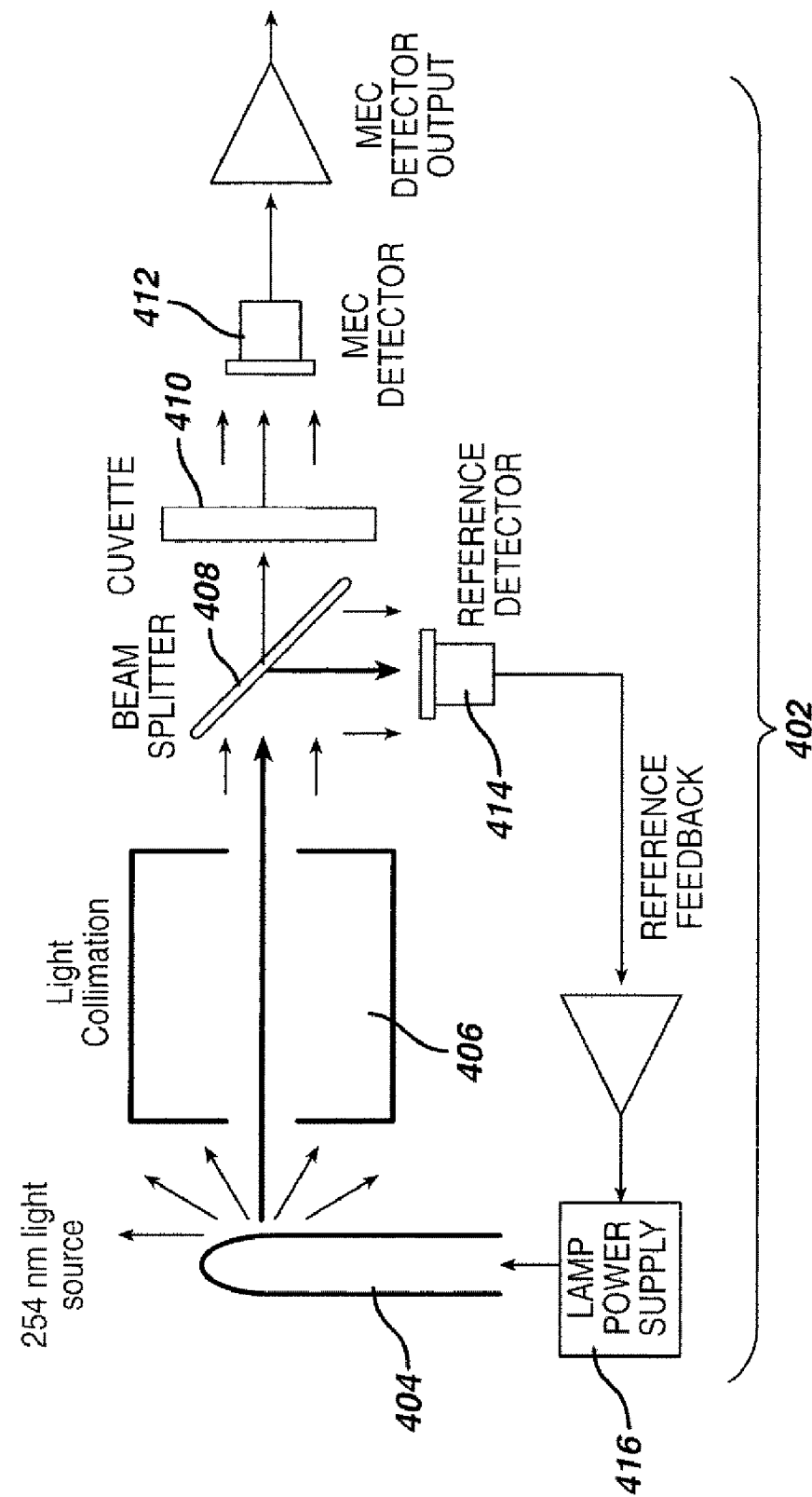
FIG. 6 is a diagrammatic illustration of an optical portion of a disinfectant concentration monitoring system.
Figure 7:
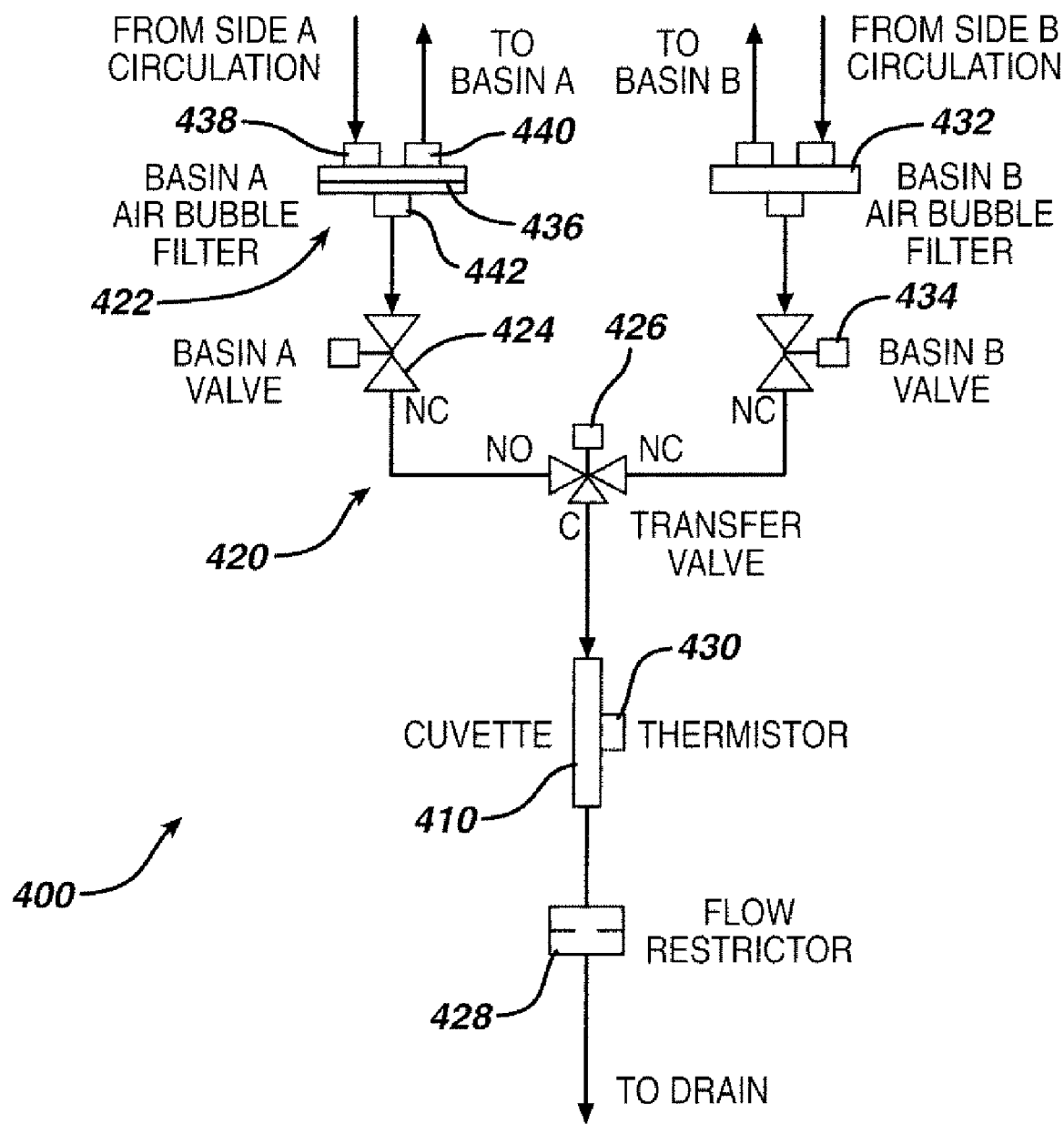
FIG. 7 is a diagrammatic illustration of a fluidics portion of the disinfectant concentration monitoring system of FIG. 6.

Turning also now to FIGS. 6 and 7, a concentration monitor subsystem 400 is shown. It monitors the concentration of the disinfectant or sterilant in the circulating fluid. A preferred active agent is ortho-phthalaldehyde (OPA). FIG. 6 shows an optical system 402 of the concentration monitor subsystem 400. It comprises a light source 404 emitting light at 254 nm through a collimator 406, a beam splitter 408 a cuvette 410 containing a sample of the circulating fluid and onto a sensor 412. The sensor 412 has an inlet filter which passes light at 254 nm plus or minus 6 nm. Preferably, the cuvette 410 is formed of optical quartz and has straight sides for minimal interference in measuring the light passing therethrough. Output from the sensor 412 is indicative of the level of OPA within the fluid. A portion of the light is reflected to a reference detector 414 to regulate a power supply 416 to the light source 404 and ensure a consistent output therefrom.

FIG. 7 shows a fluidics system 420 of the concentration monitor subsystem 400. A portion of the circulating fluid passes through a filter 422. A bubble free amount emerges from the filter 422 and passes through a first valve 424 and a selector valve 426 prior to passing into the cuvette 410. A flow restrictor 428 limits the amount of fluid to prevent undue waste and to limit flow through the filter 422. A thermistor 430 measures the temperature of the cuvette 410 to allow for temperature corrections of the reading from the sensor 412. A separate filter 432 and valve 434 are provided for the second basin.

The filter 422 is of the cross-flow type employing a 0.2 μm hydrophilic membrane 436. The maximum pore size of 0.2 μm is sufficient to keep bubbles from passing through. Fluid flows into an inlet 438 along the membrane 436 and out an outlet 440. A portion of the fluid will pass through the membrane 436 to exit a sample outlet 442 and pass to the first valve 424. In a regular filter, with just an inlet and outlet, bubbles can accumulate and block the filter requiring a complicated venting scheme to periodically unblock the filter. The filter 422 avoids this by passing bubbles out through the outlet 440. It is important to remove the bubbles as bubbles present in the cuvette 410 can lead to erroneous readings by affecting light passing through the cuvette 410.

The entire cleaning and sterilization cycle in detail comprises the following steps.

Step 1. Open the Lid

Pressing a foot pedal (not shown) opens the basin lid 16a. There is a separate foot pedal for each side. If pressure is removed from the foot pedal, the lid motion stops.

Step 2. Position and Connect the Endoscope

The insertion tube 208 of the endoscope 200 is inserted into the helical circulation tube 64. The end section 224 and head section 202 of the endoscope 200 are situated within the basin 14a, with the feed hose 222 coiled within the basin 14a with as wide a diameter as possible.

The flush lines 30, preferably color-coded, are attached, one apiece, to the endoscope openings 226, 228, 228a, 230 and 232. The air line 112 is also connected to the connector 254. A guide located on the on the station 10 provides a reference for the color-coded connections.

Step 3. Identify the User, Endoscope, and Specialist to the System

Depending on the user-selectable configuration, the control system 20 may prompt for user code, patient ID, endoscope code, and/or specialist code. This information may be entered manually (through the touch screen) or automatically such as by using an attached barcode wand (not shown).

Step 4. Close the Basin Lid

Closing the lid 16a preferably requires the user to press a hardware button and a touch-screen 22 button simultaneously (not shown) to provides a fail-safe mechanism for preventing the user's hands from being caught or pinched by the closing basin lid 16a. If either the hardware button or software button is released while the lid 16a is in the process of closing the motion stops.

Step 5. Start Program

The user presses a touch-screen 22 button to begin the washing/disinfection process.

Step 6. Pressurize the Endoscope Body and Measure the Leak Rate

The air pump is started and pressure within the endoscope body is monitored. When pressure reaches 250 mbar, the pump is stopped, and the pressure is allowed to stabilize for 6 seconds. If pressure has not reached 250 mbar in 45 seconds the program is stopped and the user is notified of the leak. If pressure drops to less than 100 mbar during the 6-second stabilization period, the program is stopped and the user is notified of the condition.

Once the pressure has stabilized, the pressure drop is monitored over the course of 60 seconds. If pressure drops more than 10 mbar within 60 seconds, the program is stopped and the user is notified of the condition. If the pressure drop is less than 10 mbar in 60 seconds, the system continues with the next step. A slight positive pressure is held within the endoscope body during the rest of the process to prevent fluids from leaking in.

Step 7. Check Connections

A second leak test checks the adequacy of connection to the various ports 226, 228, 228a, 230, 232 and the proper placement of the channel separator 240. A quantity of water is admitted to the basin 14a so as to submerge the distal end of the endoscope in the helical tube 64. Valve S1 is closed and valve S7 opened and the pumps 32 are run in reverse to draw a vacuum and to ultimately draw liquid into the endoscope channels 210 and 212. The pressure sensors 42 are monitored to make sure that the pressure in any one channel does not drop by more than a predetermined amount in a given time frame. If it does, it likely indicates that one of the connections was not made correctly and air is leaking into the channel. In any event, in the presence of an unacceptable pressure drop the control system 20 will cancel the cycle an indicate a likely faulty connection, preferably with an indication of which channel failed. For larger channels, proper connection is checked using the aforementioned method of reading the pressure of the beat frequency of pumps 32.

Pre-Rinse

The purpose of this step is to flush water through the channels to remove waste material prior to washing and disinfecting the endoscope 200.

Step 8. Fill Basin

The basin 14a is filled with filtered water and the water level is detected by the pressure sensor 59 below the basin 14a.

Step 9. Pump Water Through Channels

The water is pumped via the pumps 32 through the interior of the channels 213, 214, 217, 218, 210 and 212 directly to the drain 74. This water is not recirculated around the exterior surfaces of the endoscope 200 during this stage.

Step 10. Drain

As the water is being pumped through the channels, the drain pump 72 is activated to ensure that the basin 14a is also emptied. The drain pump 72 will be turned off when the drain switch 76 detects that the drain process is complete.

Step 11. Blow Air Through Channels

During the drain process sterile air is blown via the air pump 38 through all endoscope channels simultaneously to minimize potential carryover.

Wash

Step 12. Fill Basin

The basin 14a is filled with warm water (35° C.). Water temperature is controlled by controlling the mix of heated and unheated water. The water level is detected by the pressure sensor 59.

Step 13. Add Detergent

The system adds enzymatic detergent to the water circulating in the system by means of the peristaltic metering pump 88. The volume is controlled by controlling the delivery time, pump speed, and inner diameter of the peristaltic pump tubing.

Step 14. Circulate Wash Solution

The detergent solution is actively pumped throughout the internal channels and over the surface of the endoscope 200 for a predetermined time period, typically of from one to five minutes, preferably about three minutes, by the channel pumps 32 and the external circulation pump 70. The inline heater 80 keeps the temperature at about 35° C.

Step 15. Start Block Test

After the detergent solution has been circulating for a couple of minutes, the flow rate through the channels is measured. If the flow rate through any channel is less than a predetermined rate for that channel, the channel is identified as blocked, the program is stopped, and the user is notified of the condition. The peristaltic pumps 32 are run at their predetermined flow rates and cycle off in the presence of unacceptably high pressure readings at the associated pressure sensor 42. If a channel is blocked the predetermined flow rate will trigger the pressure sensor 42 indicating the inability to adequately pass this flow rate. As the pumps 32 are peristaltic, their operating flow rate combined with the percentage of time they are cycled off due to pressure will provide the actual flow rate. The flow rate can also be estimated based upon the decay of the pressure from the time the pump 32 cycles off.

Step 16. Drain

The drain pump 72 is activated to remove the detergent solution from the basin 14a and the channels. The drain pump 72 turns off when the drain level sensor 76 indicates that drainage is complete.

Step 17. Blow Air

During the drain process sterile air is blown through all endoscope channels simultaneously to minimize potential carryover of detergent or water which may compromise subsequent steps.

Rinse

Step 18. Fill Basin

The basin 14a is filled with warm water (35° C.). Water temperature is controlled by controlling the mix of heated and unheated water. The water level is detected by the pressure sensor 59.

Step 19. Rinse

The rinse water is circulated within the endoscope channels (via the channel pumps 32) and over the exterior of the endoscope 200 (via the circulation pump 70 and the sprinkler arm 60) for 1 minute. Also during this period a sample of water is admitted into the cuvette 410 and a baseline reading is taken by the monitoring system 400 to establish a zero value.

Step 20. Continue Block Test

As rinse water is pumped through the channels, the flow rate through the channels is measured and if it falls below the predetermined rate for any given channel, the channel is identified as blocked, the program is stopped, and the user is notified of the condition.

Step 21. Drain

The drain pump is activated to remove the rinse water from the basin and the channels.

Step 22. Blow Air

During the drain process sterile air is blown through all endoscope channels simultaneously to minimize potential carryover of water which may compromise subsequent steps.

Step 23. Repeat Rinse

Steps 18 through 22 can be repeated to ensure maximum rinsing of enzymatic detergent solution from the surfaces of the endoscope and the basin.

Disinfect

Step 24. Fill Basin

The basin 14a is filled with very warm water (53° C.). Water temperature is controlled by controlling the mix of heated and unheated water. The water level is detected by the pressure sensor 59. During the filling process, the channel pumps 32 are off in order to ensure that the disinfectant in the basin is at the in-use concentration prior to circulating through the channels.

Step 25. Add Disinfectant

A measured volume of disinfectant 92, preferably CIDEX OPA orthophalaldehyde concentrate solution, available from Advanced Sterilization Products division Ethicon, Inc., Irvine, Calif., is drawn from the disinfectant metering tube 96 and delivered into the water in the basin 14a via the metering pump 100. The disinfectant volume is controlled by the positioning of the fill sensor 98 relative to the bottom of the dispensing tube. The metering tube 96 is filled until the upper level switch detects liquid. Disinfectant 92 is drawn from the metering tube 96 until the level of the disinfectant in the metering tube is just below the tip of the dispensing tube. After the necessary volume is dispensed, the metering tube 96 is refilled from the bottle of disinfectant 92. Disinfectant is not added until the basin is filled, so that in case of a water supply problem, concentrated disinfectant is not left on the endoscope with no water to rinse it. While the disinfectant is being added, the channel pumps 32 are off in order to insure that the disinfectant in the basin is at the in-use concentration prior to circulating through the channels.

Step 26. Disinfect

The in-use disinfectant solution is actively pumped throughout the internal channels and over the surface of the endoscope, ideally for a minimum of 5 minutes, by the channel pumps and the external circulation pump. The temperature is controlled by the in-line heater 80 to about 52.5° C. During this process a sample of the circulating liquid is taken and tested for proper concentration using the concentration monitor 400. If the concentration is low, additional disinfectant can be added and the timer for this step reset.

Step 27. Flow Check

During the disinfection process, flow through each endoscope channel is verified by timing the delivering a measured quantity of solution through the channel. Valve S1 is shut, and valve S7 opened, and in turn each channel pump 32 delivers a predetermined volume to its associated channel from the metering tube 136. This volume and the time it takes to deliver provides a very accurate flow rate through the channel. Anomalies in the flow rate from what is expected for a channel of that diameter and length are flagged by the control system 20 and the process stopped.

Step 28. Continue Block Test

As disinfectant in-use solution is pumped through the channels, the flow rate through the channels is also measured as in Step 15.

Step 29. Drain

The drain pump 72 is activated to remove the disinfectant solution from the basin and the channels.

Step 30. Blow Air

During the drain process sterile air is blown through all endoscope channels simultaneously to minimize potential carryover.

Final Rinse

Step 31. Fill Basin

The basin is filled with sterile warm water (45° C.) that has been passed through a 0.2μ filter.

Step 32. Rinse

The rinse water is circulated within the endoscope channels (via the channel pumps 32) and over the exterior of the endoscope (via the circulation pump 70 and the sprinkler arm 60) for 1 minute.

Step 33. Continue Block Test

As rinse water is pumped through the channels, the flow rate through the channels is measured as in Step 15.

Step 34. Drain

The drain pump 72 is activated to remove the rinse water from the basin and the channels.

Step 35. Blow Air

During the drain process sterile air is blown through all endoscope channels simultaneously to minimize potential carryover.

Step 36. Repeat Rinse

Steps 31 through 35 are repeated two more times (a total of 3 post-disinfection rinses) to ensure maximum reduction of disinfectant residuals from the endoscope 200 and surfaces of the reprocessor.

Final Leak Test

Step 37. Pressurize the Endoscope Body and Measure Leak Rate

Repeat Step 6.

Step 38. Indicate Program Completion

The successful completion of the program is indicated on the touch screen.

Step 39. De-Pressurize the Endoscope

From the time of program completion to the time at which the lid is opened, pressure within the endoscope body is normalized to atmospheric pressure by opening the vent valve S5 for 10 seconds every minute.

Step 40. Identify the User

Depending on customer-selected configuration, the system will prevent the lid from being opened until a valid user identification code is entered.

Step 41. Store Program Information

Information about the completed program, including the user ID, endoscope ID, specialist ID, and patient ID are stored along with the sensor data obtained throughout the program.

Step 42. Print Program Record

If a printer is connected to the system, and if requested by the user, a record of the disinfection program will be printed.

Step 43. Remove the Endoscope

Once a valid user identification code has been entered, the lid may be opened (using the foot pedal as in step 1, above). The endoscope is then disconnected from the flush lines 30 and removed from the basin 14a. The lid can then be closed using both the hardware and software buttons as described in step 4, above.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof. For instance, the disinfectant concentration monitoring methods and systems disclosed herein may be useful in general instrument processing and need not be limited to endoscopes.

What is claimed is:

1. A method for measuring concentration of a germicide in an instrument processor, the method comprising the steps of:
    directing a flow of fluid containing the germicide through a bubble filter to obtain a bubble free sample of the fluid;
    directing the sample of the fluid into a sample chamber having clear sides;
    passing light of a known intensity and wavelength through the chamber and sample;
    detecting the light passing therethrough with a sensor; and
    determining a concentration of the germicide in the sample;
    wherein the bubble filter comprises a bubble outlet vent, a membrane, and a cross-flow filter wherein the flow of fluid passes along the membrane and a portion of the flow passes through the bubble outlet vent providing the sample and preventing the accumulation of bubbles against the membrane, the bubbles carried out through the bubble outlet vent.

2. The method according to claim 1 wherein the germicide comprises orthophthalaldehyde.

3. The method according to claim 2 wherein the light is at about 254 nm.

4. The method according to claim 3 wherein at least 90 percent of the light's spectra is within 450 nm plus or minus 1 nm.

5. The method according to claim 1 wherein the membrane is hydrophilic and has a maximum pore size of 0.2 µm.

6. The method according to claim 5 wherein the membrane has a maximum pore size of 0.45 µm.

7. The method according to claim 1 and further comprising the step of aborting an instrument processing cycle in the instrument processor if the concentration is below a predetermined level.

8. The method according to claim 7 wherein the germicide comprises orthophthalaldehyde and the predetermined level is 0.059% or lower.

9. The method according to claim 1 wherein the germicide comprises orthophthalaldehyde, wherein the method further comprises the step of aborting an instrument processing cycle in the instrument processor if the concentration is above 0.1%.

10. The method according to claim 1 wherein the germicide comprises orthophthalaldehyde, wherein the method further comprises the step of aborting an instrument processing cycle in the instrument processor if the concentration is above 0.85%.

11. The method according to claim 1 wherein the flow of fluid passing along the membrane carries bubbles away from an upstream side of the membrane.

12. The method of claim 1, wherein the bubble outlet vent is permanently maintained in the permanent open position.

13. An instrument processor comprising:
    an enclosure for holding an instrument;
    a fluid distribution system for delivering a fluid containing a germicide to the instrument within the enclosure;
    a germicide concentration measuring subsystem comprising:
        a bubble filter connected to the fluid distribution system;
        a sample chamber connected to a sample outlet of the bubble filter;
        a light source for passing a light of known intensity and wavelength through a sample of the fluid in the sample chamber;
        a sensor for measuring light passing through the sample;
        a control system for determining the concentration of the germicide in the sample based upon the light arriving at the sensor;
        wherein the bubble filter comprises a bubble outlet vent, a membrane, and a cross-flow filter wherein a flow of fluid passes along the membrane and a portion of the flow passes through the bubble outlet vent providing the sample and preventing the accumulation of bubbles against the membrane, the bubble outlet vent configured to carry bubbles therethrough.

14. The instrument processor according to claim 13 wherein the germicide comprises ortho-phthalaldehyde.

15. The instrument processor according to claim 4 wherein the light is at about 254 nm.

16. The instrument processor according to claim 5 wherein at least 90 percent of the light's spectra is within 254 nm plus or minus 1 nm.

17. The instrument processor according to claim 15 wherein the germicide comprises ortho-phthalaldehyde and the predetermined level is 0.059% or lower.

18. The instrument processor according to claim 13 wherein the membrane is hydrophilic and has a maximum pore size of 0.2 µm.

19. The instrument processor according to claim 18 wherein the membrane has a maximum pore size of 0.45 μm.

20. The instrument processor according to claim 13 and further comprising the control system being programmed to abort an instrument processing cycle in the instrument processor if the concentration is below a predetermined level.

21. The instrument processor according to claim 13 wherein the germicide comprises ortho-phthalaldehyde, wherein the control system is programmed to abort an instrument processing cycle in the instrument processor if the concentration is above 0.1%.

22. The instrument processor of claim 13, wherein the bubble outlet vent is permanently maintained in the permanent open position.

* * * * *